United States Patent [19]

Fuller

[11] Patent Number: 5,487,848
[45] Date of Patent: Jan. 30, 1996

[54] PREPARATION OF DIFUNCTIONAL INITIATORS FOR ANIONIC POLYMERIZATION

[75] Inventor: Timothy J. Fuller, Pittsford, N.Y.

[73] Assignee: Xerox Corporation, Stamford, Conn.

[21] Appl. No.: 279,610

[22] Filed: Jul. 25, 1994

[51] Int. Cl.$^6$ ................................ C07F 1/02; C07F 1/04; C07F 1/06
[52] U.S. Cl. ....................... 260/665 R; 585/500; 585/700
[58] Field of Search ......................... 260/665 R; 585/500, 585/700

[56] References Cited

U.S. PATENT DOCUMENTS

| | | | |
|---|---|---|---|
| 3,159,587 | 12/1964 | Uraneck et al. | 252/431 |
| 3,208,988 | 9/1965 | Forman et al. | 260/94.2 |
| 3,663,634 | 5/1972 | Morton et al. | 260/665 R |
| 3,718,702 | 2/1973 | Antkowiak | 260/665 R |
| 3,726,933 | 4/1973 | Smith et al. | 260/665 R |
| 3,862,251 | 1/1975 | Strecker | 260/665 R |
| 3,886,089 | 5/1975 | Smith, Jr. | 252/429 R |
| 4,067,917 | 1/1978 | Sigwalt et al. | 260/665 R |
| 4,172,190 | 10/1979 | Tung et al. | 526/173 |
| 4,181,684 | 1/1980 | Sigwalt et al. | 585/25 |
| 4,182,818 | 1/1980 | Tung et al. | 526/173 |
| 4,196,153 | 4/1980 | Tung et al. | 260/665 R |
| 4,201,729 | 5/1980 | Tung et al. | 260/665 R |
| 4,369,298 | 1/1983 | Kida et al. | 526/313 |
| 4,861,742 | 8/1989 | Bronstert et al. | 502/157 |
| 5,057,583 | 10/1991 | Tung et al. | 526/175 |

OTHER PUBLICATIONS

"New Perfectly Difunctional Organolithium . . . "; Guyot et al., Polymer, vol. 22, Dec. 1981; pp. 1724–1728.
"Remarks on Organodilithium Initiators"; Fetters et al.; Macro–molecules, No. 2, Mar./Apr. 1979; pp. 344–346; vol. 12.
"Anionic Polymerization"; Encyclopedia of Polymer Science and Technology; pp. 52–55 (1990).
Lucas, Organic Chemistry, Second Edition, American Book Co., New York, pp. 117, 126, 127, and 211 (1953).
Morrison et al., Organic Chemistry, 3rd Edition, Allyn and Bacon, Inc., Boston, pp. 555–559 (1973).

*Primary Examiner*—Porfirio Nazario-Gonzales
*Attorney, Agent, or Firm*—Zosan S. Soong

[57] ABSTRACT

Processes for preparing a polymerization initiator precursor compound are disclosed wherein a first process involves dimerizing a halogen-diarylpropane compound to form a tetraarylhexane compound. A second process involves reacting a diaryl-propanol compound with a halogen-diarylpropane compound to form a bis(diaryl-propyl) ether compound. A third process involves reacting a halogen-diarylpropane compound with allyl halogen to form a diaryl-hexene compound.

11 Claims, No Drawings

PREPARATION OF DIFUNCTIONAL INITIATORS FOR ANIONIC POLYMERIZATION

This invention relates generally to processes for preparing difunctional initiators and their precursors, and more particularly is directed to the preparation of difunctional initiators and their precursors derived from 3,3-diphenyl-1-propanol and/or 1-halogen-3,3-diphenylpropane, both of which are optionally substituted as described herein.

The following documents may be relevant:

Guyot et al., Vol 22, Polymer, pp. 1724–1728 (Dec. 1981), discloses difunctional organolithium initiators prepared by addition of sec or tert-butyl lithium on two families of nonpolymerizable precursors having two non-conjugated double bonds.

Fetters et al., Vol. 12, Macromolecules, No. 2, 344–346 (March-April 1979), dicloses the preparation of organodilithium initiators.

Encyclopedia of Polymer Science and Technology, "Anionic Polymerization," pp. 52–55, discloses background information on anionic polymerization.

Kida et al., U.S. Pat. No. 4,369,298, discloses 3,3,-diphenyl-1-propene (reference for example, claim 9).

Smith et al., U.S. Pat. No. 3,726,933, discloses the metallation of an alkaline earth metal with 1,1,6,6-tetraphenyl hexane (reference for example, claim 10) to form an organometallic compound useful as an polymerization catalyst.

The following documents are cited in a preliminary search report:

Uraneck et al., U.S. Pat. No. 3,159,587, discloses a lithium initiator for butadiene from 1,1-diphenylethylene, and tetraphenylethylene (reference for example, col. 2, lines 54–56).

Morton et al., U.S. Pat. No. 3,663,634, discloses the preparation of initiators involving contacting lithium with polyaryl-substituted ethylenes, hydrocarbon substituted and unsubstituted conjugated diolefins and vinyl substituted aromatic compounds.

Tung et al., U.S. Pat. No. 5,057,583, discloses a phenyl substituted multifunctional lithium initiator for the anionic polymerization of styrene/butadiene block copolymers.

Tung et al., U.S. Pat. No. 4,201,729, discloses multifunctional initiators containing lithium which are prepared by reacting a compound such as an organolithium with an organic compound containing at least two 1,1-diphenylethylene groups.

Strecker et al., U.S. Pat. No. 3,862,251, discloses an organodilithium polymerization initiator, such as the addition product of sec-butyllithium and m-divinylbenzene, which is especially applicable for the polymerization of conjugated dienes to form high 1,4-steric configuration polymers.

The preliminary search report indicates that the following documents may be of collateral or background interest: Forman et al., U.S. Pat. No. 3,208,988; Antkowiak, U.S. Pat. No. 3,718,702; Smith, U.S. Pat. No. 3,886,089; Sigwalt et al., U.S. Pat. No. 4,067,917; Tung et al., U.S. Pat. No. 4,172,190; Sigwalt et al., U.S. Pat. No. 4,181,684; Tung et al., U.S. Pat. No. 4,182,818; Tung et al., U.S. Pat. No. 4,196,153; and Bronstert et al., U.S. Pat. No. 4,861,742.

SUMMARY OF THE INVENTION

It is an object of the invention to provide processes for the preparation of difunctional initiators and their precursors.

It is another object in embodiments to provide low cost, simple processes for the preparation of difunctional initiators and their precursors.

It is still another object to provide processes for the preparation of difunctional initiators and their precursors using as the starting reactant 3,3-diphenyl propanol or 1-halogen-3,3-diphenylpropane, both optionally substituted as described herein.

A further object is to use the initiators prepared by the processes of the present invention to initiate polymerization of one or more monomers typically used as toner resins.

These objects and others may be accomplished in embodiments by a process comprising:

(a) dimerizing a halogen-diarylpropane compound to form a tetraarylhexane compound;

(b) reacting a diaryl-propanol compound with a halogen-diarylpropane compound to form a bis(diaryl-propyl) ether compound; or (c) reacting a halogen-diarylpropane compound with allyl halogen to form a diaryl-hexene compound;

wherein in (a), (b), and (c), the aryl groups optionally independently contain a substituent $R_{(a)}$, wherein a is an integer of from 1 to 5, and R is an ether having from 2 to 25 carbon atoms, an alkoxy having from 1 to 25 carbon atoms, or an aliphatic hydrocarbon having from 1 to 25 carbon atoms.

In embodiments of the invention, there is also provided a process comprising:

(a) dimerizing a 1-halogen-3,3-diphenylpropane compound to form a 1,1,6,6-tetraphenylhexane compound;

(b) reacting a 3,3-diphenyl-1-propanol compound with a 1-halogen-3,3-diphenylpropane compound to form a bis(3,3-diphenyl-1-propyl) ether compound; or (c) reacting a 1-halogen-3,3-diphenylpropane compound with allyl halogen to form a 6,6-diphenyl-1-hexene compound.

DETAILED DESCRIPTION

For simplicity, the invention will now be discussed in terms of preferred embodiments wherein the aryl groups of the reactants and products are unsubstituted phenyl groups and wherein substituent positions are provided, e.g., 1,1,6,6-tetraphenylhexane. However, it is understood that the aryl groups may be phenyl, naphthalene, anthracene, and the like. Moreover, the aryl groups may be the same or different from one another. The aryl groups are optionally substituted in the same or different manner from one another. The substitution of the aryl groups of the products may correspond to the substitution of the reactants. In addition, although preferred substituent positions are provided, other suitable positions are contemplated in the present invention. For example, the halogen of halogen-diarylpropane may be in the 1, 2, or 3 position.

The precursors for the polymerization initiators may be prepared by a variety of reactions. In one class of reactions, 1-halogen-3,3-diphenylpropane is dimerized under any suitable conditions, preferably Grignard reaction conditions or Wurtz reaction conditions, to form 1,1,6,6-tetraphenylhexane. Grignard type and Wurtz type reactions are well known. In embodiments of the present invention, 1,1,6,6-tetraphenylhexane may be prepared by adding, with stirring, 1-halogen-3,3-diphenylpropane to an organic solvent and a metal catalyst. The resulting suspension is then boiled at reflux for about 1 hour to about 6 hours at a temperature of from about 70° C. to about 150° C. and then stirred at a temperature from about 15° C. to about 50° C. for about 10 hours to about 24 hours. The tetraphenylhexane compound is isolated using any suitable purification techniques including extraction with water and methylene chloride, filtration, and evaporation of the solvent using a rotary evaporator, and the like. Any suitable organic solvent in an effective amount may be used such as tetrahydrofuran and the like. Any suitable metal catalyst may be used such as magnesium and the like. The metal catalyst employed in the reaction may be used in any effective amount, preferably from about 0.2 mole to about 2 moles of the metal per mole of 1-halogen-3,3-diphenylpropane. The compound 1-halogen-3,3-diphenylpropane may be used in any effective amount, preferably from about 0.2 mole to about 2 moles of 1-halogen-3,3-diphenylpropane per mole of the metal catalyst.

In a second class of reactions, bis(3,3-diphenyl-1-propyl) ether may be prepared by reacting 3,3-diphenyl-1-propanol with 1-halogen-3,3-diphenylpropane under ether synthesis conditions. In one embodiment, the reaction between the two compounds is conducted in an organic solvent, optionally in the presence of pyridine. The reaction mixture is boiled at reflux for about 10 hours to about 24 hours at a temperature of from about 70° C. to about 150° C. and then chilled to from about −20° C. to about 10° C. for about 30 minutes to about 2 hours. The ether compound is isolated using any suitable purification techniques including extraction with water and methylene chloride, filtration, and evaporation of the solvent using a rotary evaporator, and the like. Any suitable organic solvent may be used such as methylene chloride. Pyridine may be used in any effective amount, preferably from about 0.2 mole to about 1 mole of pyridine per mole of the propanol compound. The 1-halogen-3,3-diphenylpropane and 3,3-diphenyl-1-propanol may be used in any effective amounts, preferably from about 0.5 mole to about 2 moles of 1-halogen-3,3-diphenylpropane per mole of the propanol compound.

In another embodiment of the present invention, the bis(3,3-diphenyl-1-propyl) ether compound is prepared by halogenating/dehydrating 3,3-diphenyl-1-propanol to form 1-halogen-3,3-diphenylpropane. The resulting 1-halogen-3,3-diphenylpropane compound reacts with the remaining 3,3-diphenyl-1-propanol compound to form the ether compound. The process of this embodiment permits the preparation of bis(3,3-diphenyl-1-propyl) ether and 1-halogen-3,3-diphenylpropane and both compounds typically may be present at the end of the reaction. In this embodiment, an organic solvent, a halogenating agent, and optionally pyridine are mixed together, brought to reflux at a temperature of from about 70° C. to about 150° C. and 3,3-diphenyl-1-propanol is added. The mixture is boiled at reflux for about 10 hours to about 24 hours at a temperature of from about 70° C. to about 150° C. and then chilled to from about −20° C. to about 10° C. for about 30 minutes to about 2 hours. The 1-halogen-3,3-diphenylpropane compound and the ether compound may be isolated using any suitable purification techniques including extraction with water and methylene chloride, filtration, evaporation of the solvent using a rotary evaporator, and distillation, and the like. Any suitable organic solvent may be used such as methylene chloride. Pyridine may be used in any effective amount, preferably from about 0.2 mole to about 2 moles of pyridine per mole of the propanol compound. The halogenating agent may be any suitable agent including thionyl chloride, $PCl_5$, $POCl_3$, and the like, and mixtures thereof. The halogenating agent may be used in any effective amount, preferably from about 0.2 mole to about 2 moles of the halogenating agent per mole of the propanol compound. The propanol compound may be used in any effective amount, preferably from about 0.2 mole to about 2 moles of the propanol compound per mole of the halogenating agent.

In a preferred embodiment, 1-halogen-3,3-diphenylpropane, which is used as a reactant in certain embodiments described herein, may be prepared by the halogenating/ dehydrating of 3,3-diphenyl-1-propanol as described herein.

In a third class of reactions, 6,6-diphenyl-1-hexene is prepared by reacting 1-halogen-3,3-diphenylpropane and allyl halogen under Grignard type conditions. Grignard reactions are well known as discussed herein. In embodiments of the present invention, 1-halogen-3,3-diphenylpropane is added to an organic solvent and magnesium and the mixture is boiled at reflux at a temperature of from about 70° C. to about 150° C. for about 1 hour to about 6 hours, at the end of which most or all of the magnesium has reacted. Then, allyl halogen is added to the reaction mixture at about 15° C. to about 50° C. and the solution is stirred at about 15° C. to about 50° C. for about 10 to about 24 hours. In addition to the resulting 6,6-diphenyl-1-hexene, a byproduct in certain embodiments is 1,1,6,6-tetraphenylhexane which results when 1-halogen-3,3-diphenylpropane dimerizes in the reaction mixture. Thus, in certain embodiments, both 1,1,6,6-tetraphenylhexane and 6,6-diphenyl-1-hexene may be obtained by embodiments of the present invention. The 6,6-diphenyl-1-hexene and/or 1,1,6,6-tetraphenylhexane may be isolated using any suitable purification techniques including extraction with water and methylene chloride, filtration, evaporation of the solvent using a rotary evaporator, and chromatography separation, and the like. Any suitable organic solvent may be employed such as tetrahydrofuran. Magnesium may be employed in any effective amount, preferably from about 0.2 mole to about 2 moles of magnesium per mole of 1-halogen-3,3-diphenylpropane. Ally halogen and 1-halogen-3,3-diphenylpropane may be employed in any effective amount, preferably from about 1 mole to about 2 moles of allyl halogen per mole of 1-halogen-3,3-diphenylpropane.

It is believed that under Grignard conditions, 1-halogen-3,3-diphenylpropane reacts with magnesium to form a compound of diphenylpropane-Mg-halogen. It is this intermediate compound which is believed to react with the allyl halogen to form 6,6-diphenyl-1-hexene. However, it is understood that the phrase "reacting a halogen-diarylpropane compound with allyl halogen to form a diaryl-hexene" and similar phrases as used herein encompass this situation.

The term halogen as used herein includes bromine, chlorine, and iodine. It is preferred that the halogen is chlorine, e.g., 1-chloro-3,3-diphenylpropane, allyl chloride and the like.

The difunctional initiators are formed by reacting the precursor compounds produced by processes of the present invention with a metallation compound selected for example from organometallic compounds and alkali metals. In a preferred embodiment, the precursor compound is added to a hydrocarbon solvent containing the organometallic compound or the alkali metal under mild agitation conditions, or vigorous agitation, if desired, in an inert atmosphere such as argon, helium, krypton, xenon, neon, methane, ethane and the like. The time required for formation of the initiator compound depends upon various factors such as temperature, rate of agitation, ratio of reactants, and the like. In general, the time required is in the range of from about 10 minutes to 100 hours or longer. The temperature for the reaction generally ranges from about −20° C. to about 100°

C. The organometallic compound or alkali metal is added in any effective amount, preferably in excess, more preferably from about 2 mole to about 6 moles of the organometallic compound or alkali metal per mole of the precursor compound. The alkali metal includes lithium, sodium, potassium and the like. The metallic component of the organometallic compound may be any effective metal, preferably an alkali metal as described herein. The organic component of the organometallic compound may be any effective organic moiety sufficiently basic to extract the hydrogen from the carbon atom bonded to the diaryl groups (e.g., diphenyl groups). Preferably, the organic component of the organometallic compound is a hydrocarbon containing 1 to about 25 carbon atoms including ethyl, propyl, isopropyl, n-butyl, sec-butyl, tert-butyl, pentyl, hexyl, napthalene and the like and an amine including $NH_2$, $N(ethyl)_2$, and the like. Preferred organometallic compounds are $LiNH_2$, $LiN(ethyl)_2$, n-butyl, sec-butyl, or tert-butyllithium, and naphthalene lithium. The alkali metal may be in the form of a sand, chunks, wire, shot, mixtures thereof, and the like.

Any suitable organic solvent may be employed to prepare the initiator compounds including hydrocarbon solvents, and/or etheric solvents. Suitable hydrocarbon solvents include aliphatic of 1 to about 25 carbon atoms, cycloaliphatic or aromatic hydrocarbons such as pentane, hexane, cyclohexane, cycloctane, benzene, toluene, and the like, and mixtures thereof. Suitable etheric solvents include methyl phenyl ether, ethyl phenyl ether, diphenyl ether, dibiphenyl ether, allyl 2-naphthyl ether, allyl phenyl ether, allyl 2-tolyl ether, and the like, and mixtures thereof.

With the precursor compound tetraarylhexane such as 1,1,6,6-tetraphenylhexane, the corresponding difunctional initiator is of the formula

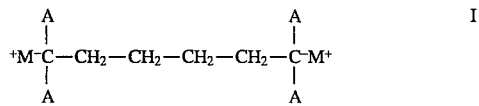

wherein the substituents are as defined herein.

With the precursor compound bis(diaryl-propyl) ether such as bis(3,3-diphenyl-1-propyl) ether, the corresponding difunctional initiator is of the formula II

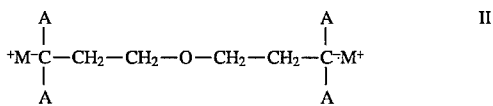

wherein the substituents are as defined herein.

With the precursor compound diaryl-hexane such as 6,6-diphenyl-1-hexene, the corresponding difunctional initiator is of the formula IIIA and/or IIIB

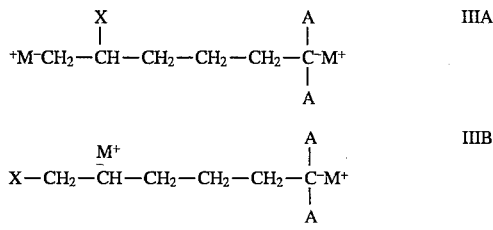

wherein the substituents are as defined herein.

In the above formulas I, II, IIIA, and IIIB, A is an aryl optionally and independently substituted by $R_{(a)}$. The substituent A is an aryl such as phenyl, naphthalene, anthracene, and the like. Also, for the optional substituent $R_{(a)}$, a is an integer of from 1 to 5, and R is an ether having from 2 to 25 carbon atoms, an alkoxy having from 1 to 25 carbon atoms, or an aliphatic hydrocarbon having from 1 to 25 carbon atoms. In addition, in the formulas, $M^+$ is an alkali metal or the metallic component of the organometallic compound as described herein; and X is the organic component of the organometallic compound such as a hydrocarbon or an amine as described herein. Typical processes to prepare initiator compounds are illustrated in Sigwalt et al., U.S. Pat. No. 4,181,684; Antkowiak, U.S. Pat. No. 3,718,702; and Uraneck et al., U.S. Pat. No. 3,159,587, the disclosures of which are totally incorporated by reference.

The initiator compounds prepared by embodiments of the present invention may be employed to initiate the anionic polymerization of dienes including butadiene, acrylates and vinyl monomers including styrene, and the like, and mixtures thereof. The polymerization reaction is performed in any of the organic solvents discussed herein used in the preparation of the precursors and initiators and any others typically used in polymerization reactions. The desired monomer or monomers including styrene monomer and butadiene monomer are added to the final organic solution in the preparation of the initiator and polymerization occurs. Alternatively, if the initiator has already been isolated, it is again dissolved in a suitable organic solvent and the desired monomer or monomers are added. In either procedure, external heat or other catalysts may optionally be employed. The quantity of the initiator which is employed in the polymerization process may be in any effective amount and is dependent upon the quantity of monomer used in the process, which in turn is dependent upon the desired molecular weight for the ultimate polymer end product. Preferably, the initiator is employed in an amount from about 0.2 mole to about 2 moles of the initiator per mole of monomer. The organic solvent may be present in any suitable concentration and may be employed in amounts in which the final polymer product will comprise about 20 percent by weight. It is believed that the initiator becomes part of the polymer chain during polymerization. Anionic polymerizations are illustrated in Tung et al., U.S. Pat. No. 4,431,777, and Tung et al., U.S. Pat. No. 4,427,837, Strecker, U.S. Pat. No. 3,862,251, the disclosures of which are totally incorporated by reference.

The invention will now be described in detail with respect to specific preferred embodiments thereof, it being understood that these examples are intended to be illustrative only and the invention is not intended to be limited to the materials, conditions or process parameters recited herein. All percentages and parts are by weight unless otherwise indicated.

EXAMPLE 1

Preparation of 1-Chloro-3,3-Diphenylpropane and Bis(3,3-diphenyl-1-propyl) ether To a 1-liter, 3-neck round-bottom flask equipped with an argon inlet, mechanical stirrer and addition funnel were added methylene chloride (150 mL), thionyl chloride (30 g) and pyridine (20 mL). There was fuming evident when the pyridine was added to the thionyl chloride. The mixture was brought to reflux in an oil bath, and 3,3-diphenyl-1-propanol (50 g) was added in methylene chloride (110 mL) over 45 min with an addition funnel. After complete addition, the mixture was boiled at reflux for 16 hours and then chilled to 0° C. to allow crystallization of the pyridinium hydrochloride formed during the reaction. The mixture was filtered, and the solvent was removed from the filtrate to yield 69.92 grams of liquid. The liquid, collected by Kugelrohr distillation at 120° C. between 0.4 to 0.1 mm mercury, was identified by $^1$H and $^{13}$C NMR spectrometry as 1-chloro-3,3-diphenylpropane. The yield was 22.41 grams (44.8%). The residue (still bottoms) was a viscous, light yellow oil identified by $^1$H and $^{13}$C NMR spectrometry as bis(3,3-diphenyl-1-propyl) ether.

EXAMPLE 2

Preparation of 1,1,6,6-Tetraphenylhexane by Grignard Coupling Reaction of 1-Chloro-3,3-Diphenylpropane with Itself To a 500-mL flask equipped with reflux condenser, argon inlet, mechanical stirrer, and an addition funnel, were added tetrahydrofuran (50 mL) and magnesium turnings (1.41 g, 0.0578 mol). To this stirred suspension was added with the addition funnel, 1-chloro-3,3-diphenylpropane (22.19 g, 0.0963 mol) in tetrahydrofuran (75 mL). The suspension turned from light yellow to bright dark yellow after boiling at reflux for 1 hour. After 3 hours boiling at reflux, the reaction mixture was stirred at 25° C. for 16 hours. The reaction mixture was filtered under argon with a Schlenck funnel, and the solvent was removed from the filtrate using a rotary evaporator. The residue was treated with water (100 mL) and extracted with methylene chloride (500 mL). The methylene chloride layer was dried over sodium sulfate, filtered and evaporated using a rotary evaporator. An oily crystalline residue remained which was dissolved in a minimum amount of hexanes and passed through a chromatography column packed with activity 1 neutral alumina by elution with hexanes. The crystalline fractions obtained on evaporation of the hexanes were then recrystallized from hexanes to yield a white crystalline product which had a liquid crystalline melting temperature range between 113° and 118° C. and demonstrated $^1$H and $^{13}$C NMR spectra consistent with the structure 1,1,6,6-tetraphenylhexane.

EXAMPLE 3

Preparation of 6,6-diphenyl-1-hexene by Grignard Reaction of 1-Chloro-3,3-Diphenylpropane with Allyl Chloride Tetrahydrofuran (50 mL) and magnesium turnings (2.81 g, 0.116 mol) were added to a 1-liter, 3-neck round bottom flask equipped with an argon inlet, reflux condenser, mechanical stirrer, and addition funnel. With an addition funnel, 1-chloro-3,3-diphenylpropane (22.19 g, 0.0963 mol) were added and the suspension was brought to reflux. The suspension turned from light yellow to bright dark yellow after 1 hour reflux. After 3 hours boiling at reflux, most of the magnesium had reacted, and allyl chloride (8.86 mL) was added over 10 minutes to the reaction mixture at 25° C. The reaction mixture boiled at reflux during the addition due to an exothermic reaction. The solution was allowed to stir at 25° C. for 16 hours. Solvent was removed from the reaction mixture using a rotary evaporator, and then water (200 mL) and methylene chloride (500 mL) were added to the residue. The methylene chloride layer was separated, dried over sodium sulfate, filtered and then removed using a rotary evaporator. An oily crystalline residue remained which was dissolved in a minimum amount of hexanes and passed through a chromatography column packed with activity 1 neutral alumina by elution with hexanes. The first several fractions contained 6,6-diphenyl-1-hexene, obtained as a clear, viscous oil after the hexanes had evaporated. Later, fractions contained 1,1,6,6-tetraphenyhexane obtained as a white crystalline solid with a melting point between 114° and 118° C., after the hexanes had evaporated. Products were analyzed using $^1$H and $^{13}$C NMR spectrometry.

EXAMPLE 4

Preparation of Styrene-Butadiene Copolymer with Bis(3,3-diphenyl-1-propyl) Ether and 2-Equivalents of n-Butyllithium.

A 1-liter beverage bottle was equipped with a stir bar and rubber septum. The bottle was washed with n-butyllithium (15 mL) in cyclohexane (100 mL) and then rinsed with cyclohexane (100 mL) using a double-ended needle to add and remove reagents. After an argon purge, bis(3,3-diphenyl-1-propyl) ether (0.0116 mol) in cyclohexane (350 mL, 268.1 g) was added by cannula under argon, followed by n-butyllithium (0.0237 mol) added via syringe. The solution became bright red. Tetrahydrofuran (300 mL, 262.7 g) was added. After cooling the beverage bottle reactor in a dry ice/2-propanol bath at −30° C., styrene (100 mL, 91.6 g) and butadiene (29.1 g, 43 mL) combined were added over 5 minutes under argon. After 16 hours, methanol (10 mL) was added to the red reaction solution by syringe and the reaction mixture became colorless. The reaction mixture was added to 2-propanol (1-gallon) using a Waring blender to precipitate the polymer. The polymer was isolated by filtration, washed with methanol (1 L), and vacuum dried to yield 116 g of styrene-butadiene copolymer (96% yield). The resultant white polymer was comprised of 77.8 wt. % styrene and 22.2 wt. % butadiene with 78.8% of the butadiene content as the 1,2-vinyl regioisomer, as determined using $^1$H NMR spectrometry. The monomodal GPC $M_w/M_n$ was 28,690/18,710, and the glass transition temperature was 50.9° C. as determined by differential scanning calorimetry. The copolymer product was made into toner by extrusion at 130° C. with 6 wt. % Regal 330 carbon black and 2 wt. % cetyl pyridium chloride charge contol agent followed by micronization. The MFT (Minimum Fusing Temperature) of the resulting toner was 125° C. and the HOT (Hot Offset Temperature) was 145° C. using a Xerox 5028™ silicone elastomer roll fuser operated at 3.3 inches per second.

COMPARATIVE EXAMPLE 5

Preparation of Lithium/Naphthalene Catalyst.

To a 1-liter, one-neck flask were added naphthalene (45 g) and lithium shot (5.1 g) in mineral oil. The flask was equipped with a magnetic stir bar, and was then capped with a rubber septum. After an argon purge, freshly distilled tetrahydrofuran (300 mL) was then added by cannula under argon and the mixture was stirred for 16 hours. The molarity of this initiator solution was about 2.38 molar, as determined by an average of the GPC (Gel Permeation Chromatography) molecular weight results. Lithium/naphthalene catalyst made as described above is typically between 1.9 and 2.6 Molar.

COMPARATIVE EXAMPLE 6

Preparation of Styrene-Butadiene Copolymer with Lithium/Naphthalene Catalyst.

A 1-liter beverage bottle was equipped with a stir bar and rubber septum. After an argon purge, tetrahydrofuran (300 mL, 262.7 g) and cyclohexane (350 mL, 268.1 g) were added by cannula under argon. Lithium/naphthalene initiator solution (approximately 0.5 mL) was added dropwise until the solution was light yellow-green. More 2.38 molar lithium/naphthalene solution (11 mL) was then added by syringe. After cooling the beverage bottle reactor in a dry ice/2-propanol bath at −30° C., styrene (100 mL, 91.6 g) and butadiene (29.1 g, 43 mL) combined were added over 5 minutes under argon. After 16 hours, methanol (10 mL) was added to the red reaction solution by syringe and the reaction mixture became colorless. The reaction mixture was added to 2-propanol (1-gallon) using a Waring blender to precipitate the polymer. The polymer was isolated by filtration, washed with methanol (1 L), and vacuum dried to yield 116 g of styrene-butadiene copolymer (96% yield). The resultant white polymer was comprised of 77.52 wt. % styrene and 22.48 wt. % butadiene with 78.1% of the butadiene content as the 1,2-vinyl regioisomer, as determined using $^1$H NMR spectrometry. The monomodal GPC $M_w/M_n$ was 26,162/18,499, and the glass transition temperature was 50.3° C. as determined by differential scanning calorimetry. The copolymer product was made into toner by extrusion at 130° C. with 6 wt. % Regal 330 carbon black and 2 wt. % cetyl pyridium chloride charge contol agent followed by micronization. The MFT of the resulting toner was 124° C. and the HOT was 146° C. using a Xerox Corporation 5028™ silicone elastomer roll fuser operated at 3.3 inches per second.

Other modifications of the present invention may occur to those skilled in the art based upon a reading of the present disclosure and these modifications are intended to be included within the scope of the present invention.

I claim:

1. A process comprising dimerizing a 1-halogen-3,3-diphenylpropane compound to form a 1,1,6,6-tetraphenylhexane compound.

2. The process of claim 1, wherein the halogen in the 1-halogen-3,3-diphenylpropane compound is chlorine.

3. The process of claim 1, further comprising reacting the 1,1,6,6-tetraphenylhexane compound with an organometallic compound or an alkali metal to form a first polymerization initiator compound.

4. A process comprising reacting a 3,3-diphenyl-1-propanol compound with a 1-halogen-3,3-diphenylpropane compound to form a bis(3,3-diphenyl-1-propyl) ether compound, and reacting the bis(3,3-diphenyl-1-propyl) ether compound with an organometallic compound or an alkali metal to form a second polymerization initiator compound.

5. The process of claim 4, wherein the halogen in the 1-halogen-3,3-diphenylpropane compound is chlorine.

6. A process comprising reacting a 1-halogen-3,3-diphenylpropane compound with allyl halogen to form a 6,6-diphenyl-1-hexene compound, and reacting the 6,6-diphenyl-1-hexene compound with an organometallic compound to form a third polymerization initiator compound.

7. The process of claim 6, wherein the halogen in the 1-halogen-3,3-diphenylpropane compound and the allyl halogen is chlorine.

8. A process comprising dimerizing a halogen-diarylpropane compound to form a tetraarylhexane compound, wherein the aryl groups of the tetraarylhexane compound optionally independently contain a substituent $R_{(a)}$, wherein a is an integer of from 1 to 5, and R is an ether having from 2 to 25 carbon atoms, an alkoxy having from 1 to 25 carbon atoms, or an aliphatic hydrocarbon having from 1 to 25 carbon atoms.

9. The process of claim 8, further comprising reacting the tetraarylhexane compound with an organometallic compound or an alkali metal to form a first polymerization initiator compound.

10. A process comprising reacting a diaryl-propanol compound with a halogen-diarylpropane compound to form a bis(diaryl-propyl) ether compound, wherein the aryl groups of the ether compound optionally independently contain a substituent $R_{(a)}$, wherein a is an integer of from 1 to 5, and R is an ether having from 2 to 25 carbon atoms, an alkoxy having from 1 to 25 carbon atoms, or an aliphatic hydrocarbon having from 1 to 25 carbon atoms; and reacting the ether compound with an organometallic compound or an alkali metal to form a second polymerization initiator compound.

11. A process comprising reacting a halogen-diarylpropane compound with allyl halogen to form a diaryl-hexene compound, wherein the aryl groups of the diaryl-hexene compound optionally independently contain a substituent $R_{(a)}$, wherein a is an integer of from 1 to 5, and R is an ether having from 2 to 25 carbon atoms, an alkoxy having from 1 to 25 carbon atoms, or an aliphatic hydrocarbon having from 1 to 25 carbon atoms; and reacting the diaryl-hexene compound with an organometallic compound to form a third polymerization initiator compound.

* * * * *